US007771609B2

(12) United States Patent
Leventis et al.

(10) Patent No.: US 7,771,609 B2
(45) Date of Patent: Aug. 10, 2010

(54) METHODS AND COMPOSITIONS FOR PREPARING SILICA AEROGELS

(75) Inventors: Nicholas Leventis, Westlake, OH (US); Chariklia Leventis, Westlake, OH (US)

(73) Assignee: Aerogel Technologies, LLC, Glendale, WI (US)

( * ) Notice: Subject to any disclaimer, the term of this patent is extended or adjusted under 35 U.S.C. 154(b) by 68 days.

(21) Appl. No.: 10/643,578

(22) Filed: Aug. 18, 2003

(65) Prior Publication Data

US 2004/0132846 A1 Jul. 8, 2004

Related U.S. Application Data

(60) Provisional application No. 60/405,693, filed on Aug. 22, 2002, provisional application No. 60/404,032, filed on Aug. 16, 2002.

(51) Int. Cl.
*C01B 33/12* (2006.01)
(52) U.S. Cl. .......................... 252/62; 423/335; 423/338; 427/220; 501/12; 516/101
(58) Field of Classification Search .................. 516/101; 252/62; 423/335, 338; 427/220; 501/12
See application file for complete search history.

(56) References Cited

U.S. PATENT DOCUMENTS

| 5,502,082 | A | 3/1996 | Unger et al. |
| 5,541,234 | A | 7/1996 | Unger et al. |
| 5,990,184 | A | 11/1999 | Biesmans |
| 6,300,385 | B1 * | 10/2001 | Hashida et al. ............... 521/82 |
| 6,364,953 | B1 * | 4/2002 | Kawakami et al. .......... 118/665 |
| 6,428,898 | B1 * | 8/2002 | Barsotti et al. .............. 428/447 |

OTHER PUBLICATIONS

Katti, Atul, et al., "Chemical, physical and mechanical characterization of isocyanate cross-linked amine-modified silica aerogels", *Chem. Mater., ASAP*, Article No. 10.1021/cm0513841 S0897-4756(05)01384-0,(Jun. 2005),12 pgs.
Leventis, Nicholas, et al., "Nanoengineering strong silica aerogels", *Nano Letters*, 2(9), (2002),957-60.
Zhang, Guohui, et al., "Isocyanate-crosslInked silica aerogel monoliths: preparation and characterization", *Journal of Non-Crystalline Sodids 350*, (2004),152-64.
Armand, A. C., et al., "Caractérisation Acoustique et Mécanique des Aérogels de Silice [Acoustic and Mechanical Characterization of Silica Aerogels]", *Journal de Physique IV, Colloque C1. supplément au Journal de Physique III*, vol. 2, (1992), C1-759-C1-762.
Brüesch, P., et al., "Electrical and Infrared Dielectrical Properties of Silica Aerogels and of Silica-Aerogel-Based Composites", *Applied Physics A—Solids and Surfaces*, (1993), 329-337.
Büttner, D., et al., "Thermal Loss Coefficients of Low-Density Silica Aerogel Tiles", *Solar Energy*, 40(1), (1988), 13-15.
Caps, R., et al., "Thermal Transport in Monolithic Silica Aerogel", *Revue de Physique Appliquée, Colloque C4, supplément au No. 4*, (1989), C4-113-C4-118.

Courtens, E., et al., "Structure and Dynamics of Silica Aerogels", *Philosophical Magazine B*, 65(2), (1992), 347-355.
Cross, J., et al., "Mechanical Properties of $SiO_2$—Aerogels", *Revue de Physique Appliquée, Colloque C4, Supplement au No. 4*, (1989), C4-185-C4-190.
Da Silva, A., et al., "Properties of Water Adsorbed in Porous Silica Aerogels", *Journal of Non-Crystalline Solids*, 145, (1992), 168-174.
Damrau, U., et al., "$^{29}Si$ MAS-NMR Investigations of Silica Aerogels", *Journal of Non-Crystalline Solids*, 145, (1992), 164-167.
Devreux, F., et al., "NMR Determination of the Fractal Dimension in Silica Aerogels", *Physical Review Letters*, 65(5), (1990), 614-617.
Ehrburger-Dolle, F., et al., "Relations Between the Texture of Silica Aerogels and Their Preparation", *Journal of Non-Crystalline Solids*, 186, (1995), 9-17.
Emmerling, A., et al., "Relationship Between Optical Transparency and Nanostructural Features of Silica Aerogels", *Journal of Non-Crystalline Solids*, 185, (1995), 240-248.
Emmerling, A., et al., "Structural Modifications of Highly Porous Silica Aerogels Upon Densification", *J. Appl. Cryst.*, 24 (1991), 781-787.
Gross, J., et al., "Mechanical Properties of $SiO_2$ Aerogels", *J. Phys. D: Appl. Phys.*, 21, (1988), 1447-1451.
Gross, J., et al., "Ultrasonic Evaluation of Elastic Properties of Silica Aerogels", *Materials Science and Engineering A*, 168, (1993), 235-238.
Gross, J., et al., "Ultrasonic Velocity Measurements in Silica, Carbon and Organic Aerogels", *Journal of Non-Crystalline Solids*, 145, (1992), 217-222.
Hdach, H., et al., "Effect of Aging and pH on the Modulus of Aerogels", *Journal of Non-Crystalline Solids*, 121, (1990), 202-205.
Hench, L. L., et al., "The Sol-Gel Process", *Chemical Reviews*, 90(1), (1990), 33-72.
Hrubesh, L. W., et al., "Thermal Properties of Organic and Inorganic Aerogels", *J. Mater. Res.*, 9(3), (1994), 731-738.
Hrubesh, L. W., et al., "Thin Aerogel Films for Optical, Thermal, Acoustic, and Electronic Applications", *UCRL-JC-117553 Preprint, International Symposium on Aerogels 4*, (Sep. 19-21, 1994, Berkeley, CA),(Sep. 1994), 17 pgs.
Husing, N., et al., "Aerogels—Airy Materials: Chemistry, Structure, and Properties", *Angewandt Chemie International Edition*, 37, (1998), 22-45.
Jang, K. Y., et al., "Study of Sol-Gel Processing for Fabrication of Hollow Silica-Aerogel Spheres", *J. Vac. Sci. Technol. A*, 8(3), (May/Jun. 1990), 1732-1735.
Kim, N. K., et al., "Fabrication of Hollow Silica Aerogel Spheres by a Droplet Generation Method and Sol-Gel Processing", *J. Vac. Sci. Technol. A*, 7(3), (1989), 1181-1184.
Morris, C. A., et al., "Silica Sol as a Nanoglue: Flexible Synthesis of Composite Aerogels", *Science*, 284, (1999), 622-624.
Novak, B. M., et al., "Low-Density, Mutually Interpenetrating Organic-Inorganic Composite Materials via Supercritical Drying Techniques", *Chem. Mater.*, 6, (1994), 282-286.

(Continued)

*Primary Examiner*—John Cooney
(74) *Attorney, Agent, or Firm*—Wolf, Greenfield & Sacks, P.C.

(57) ABSTRACT

Cross-linked sol-gel like materials and cross-linked aerogels, as well as methods for making such cross-linked sol-gel like materials and cross-linked aerogels are described.

21 Claims, 6 Drawing Sheets

OTHER PUBLICATIONS

Pajonk, G. M., "Some Catalytic Applications of Aerogels for Environmental Purposes", *Catalysis Today*, 52, (1999), 3-13.

Phalippou, J., et al., "Fracture Toughness of Silica Aerogels", *Revue de Physique Appliquée, Colloque C4, Supplément au No. 4*, (1989), C4-191-C4-196.

Phalippou, J., et al., "Glasses From Aerogels—Part 1. The Synthesis of Monolithic Silica Aerogels", *Journal of Materials Sciences*, 25(7), (1990), 3111-3117.

Posselt, D., et al., "The Thermal Conductivity of Silica Aerogel in the Phonon, the Fracton and the Particle-Mode Regime", *Europhysics Letters*, 16(1), (1991), 59-65.

Rogacki, G., et al., "Diffusion of Ethanol-Liquid $CO_2$ in Silica Aerogel", *Journal of Non-Crystalline Solids*, 186, (1995), 73-77.

Schaefer, D. W., et al., "Structure and Topology of Silica Aerogels", *Journal of Non-Crystalline Solids*, 145, (1992), 105-112.

Sleator, T., et al., "Low-Temperature Specific Heat and Thermal Conductivity of Silica Aerogels", *Physical Review Letters*, 66(8), (1991), 1070-1073.

Tsou, P., "Silica Aerogel Captures Cosmic Dust Intact", *Journal of Non-Crystalline Solids*, 186, (1995), 415-427.

Tullo, A. H., "Stiff Competition—Long-Fiber-Reinforced Thermoplastics are Gathering Strength in Key Industries", *Chem. & Eng. News*, (Jan. 28, 2002), 21-22.

Woignier, T., et al., "Different Kinds of Fractal Structures in Silica Aerogels", *Journal of Non-Crystalline Solids*, 121, (1990), 198-201.

Woignier, T., et al., "Glasses From Aerogels. Part 2—The Aerogel-Glass Transformation", (1990), 3118-3126.

Woignier, T., et al., "Mechanical Strength of Silica Aerogels", *Journal of Non-Crystalline Solids*, 100, (1988), 404-408.

Woignier, T., et al., "Scaling Law Variation of the Mechanical Properties of Silica Aerogels", *Revue de Physique Appliquée, Colloque C4, Supplément au No. 4*, (1989), C4-179-C4-184.

Woignier, T., et al., "Section 13. Rheological, Mechanical and Other Properties—Evolution of Mechanical Properties During the Alcogel-Aerogel-Glass Process", *Journal of Non-Crystalline Solids*, 147 & 148, (1992), 672-680.

Yim, T.-J., et al., "Fabrication and Thermophysical Characterization of Nano-Porous Silica-Polyurethane Hybrid Aerogel by Sol-Gel Processing and Supercritical Solvent Drying Technique", *Korean J. Chem. Eng.* 19(1), (2002), 159-166.

* cited by examiner

METHODS AND COMPOSITIONS FOR PREPARING SILICA AEROGELS

PRIORITY CLAIM

This application claims priority from U.S. provisional applications having Ser. No. 60/404,032, filed on Aug. 16, 2002; and Ser. No. 60/405,693, filed Aug. 22, 2002, both of which are incorporated herein in their entirety.

FIELD OF THE INVENTION

The present invention relates generally to the field of aerogels. More specifically, it relates to cross-linked aerogels.

BACKGROUND OF THE INVENTION

Aerogels are chemically inert, highly porous ceramic materials. Generally, these materials are produced by forming a gel containing a solvent and a porous solid component, and then removing the solvent to leave behind the porous solid. Removal of the solvent while preserving the porous solid structure is difficult because the gel often shrinks upon removal of the solvent and causes the porous solid structure to crack and break. This obstacle has been overcome by transforming the solvent within the gel into a vapor above its supercritical point, and allowing the vapor to escape and leave the intact porous solid structure. The first true aerogels were producted by exchanging water in the gel with alcohol that was then converted to a supercritical fluid and allowed to escape. This produced an aerogel that was transparent, low density, and highly porous. A major advance took place when this technique was combined with the application of sol-gel chemistry to prepare silica aerogels. This process replaced the sodium silicate that was typically used with an alkoxysilane, (for example, tetramethyorthosilicate, TMOS). Hydrolyzing TMOS in a solution of methanol produced a gel in one step that was called an "alcogel". This eliminated two of the drawbacks of the previously used procedure, namely, the water-to-alcohol exchange step and the presence of inorganic salts in the gel. Drying these alcogels under supercritical alcohol conditions produced high-quality silica aerogels. In subsequent years, this approach was extended to prepare aerogels from a wide variety of metal oxide aerogels.

Recent advances have produced aerogels that are the product of a sol-gel process, whose final stage involves extracting the pore-filling solvent with liquid $CO_2$. The latter is gasified supercritically and is vented off, leaving behind a very low density solid (0.002-0.8 gram/$cm^{-3}$), with the same volume as the original hydrogel and a chemical composition identical to glass.

Aerogels have been considered for thermal insulation, catalyst supports, or as hosts for a variety of functional materials for chemical, electronic, and optical applications. However, practical application of aerogels has been slow because aerogels are brittle and hygroscopic. These properties cause several known aerogels to absorb moisture from the environment which causes them to collapse due to the capillary forces developing in the pores. Therefore, aerogels having superior strength characteristics that would overcome the deficiencies of the past would be useful in a large variety of applications.

SUMMARY OF THE INVENTION

The invention provides methods to prepare a cross-linked sol-gel like material comprising contacting a sol-gel like material with a cross-linking agent.

The invention also provides methods to prepare a cross-linked aerogel comprising drying a cross-linked sol-gel like material.

The invention also provides cross-linked aerogels.

Definitions

Aerogel: What remains when the liquid part of a sol-gel like material is removed without damaging the solid part (most often achieved by supercritical extraction). If made correctly, the aerogel retains the original shape of the sol-gel like material and at least 50% (typically >85%) of the sol-gel like material's volume.

The terms alkyl, alkenyl, alkynyl, denote both straight and branched groups; but reference to an individual radical such as "propyl" embraces only the straight chain radical, a branched chain isomer such as "isopropyl" being specifically referred to.

Aryl: denotes a phenyl radical or an ortho-fused bicyclic carbocyclic radical having about nine to ten ring atoms in which at least one ring is aromatic (e.g. phenyl, indenyl, or naphthyl).

Attached group: An attached group is an organic or inorganic molecule or molecules that are part of a cross-linking agent such that the attached group becomes bonded to a sol-gel like material. Examples of attached groups include, but are not limited to, absorbants, catalysts, flurophores, biomolecules, redox active labels, reactive groups such as amines, epoxides, hydroxyls, anhydrides, acylhalides, and carboxyl groups.

Condensation: A condensation reaction occurs when two metal hydroxides (M—OH+HO—M) combine to give a metal oxide species (M—O—M). The reaction forms one water molecule.

Cross-linking agent: A cross-linking agent can be an organic or an inorganic compound that forms a bond with a reactive side group accessible on a sol-gel like material to form a cross-linked sol-gel like material that can be dried to form a cross-linked aerogel.

Cross-linked aerogel: an aerogel having at least two side groups that are linked by a cross-linking agent that forms a bond with the side groups.

Gel Point: The point in time at which the network of linked oxide particles spans the container holding the Sol. At the gel point the Sol becomes a sol-gel like material.

Hydrolysis: The reaction of a metal alkoxide (M-OR) with water, forming a metal hydroxide (M-OH).

Sol: A solution of various reactants that are undergoing hydrolysis and condensation reactions. The molecular weight of the oxide species produced continuously increases. As these species grow, they may begin to link together in a three-dimensional network.

Sol-gel like material: A sol-gel material is a material that results from a sol-gel process as is known in the art and described herein. For example, a sol-gel forms a rigid substance called a sol-gel like material. The sol-gel like material can be removed from its original container and can stand on its own. A sol-gel like material consists of two parts, a solid part and a solvent part. The solid part is formed by the three-dimensional network of linked oxide particles. The solvent part fills the free space surrounding the solid part. The solvent and solid parts of a sol-gel like material occupy the same apparent volume.

Substantially: A sol-gel like material that is substantially filled with a solvent refers to a sol-gel material that is filled with at least about 75%, 80%, 90%, 95%, or 98% solvent by volume.

Supercritical fluid: A substance that is above its critical pressure and critical temperature. A supercritical fluid possesses some properties in common with liquids (density, thermal conductivity) and some in common with gases (fills its container, does not have surface tension).

DETAILED DESCRIPTION OF THE INVENTION

In one example, the invention provides silica aerogel monoliths wherein the strength has been improved by a factor of over 100 through cross-linking the nanoparticle building blocks of preformed silica hydrogels with a cross-linking agent, such as poly(hexamethylene diisocyanate). The composite monoliths of the invention offer the advantage that they are much less hygroscopic than native silica, and they do not collapse when contacted with liquids.

Figures 2A, 2B:
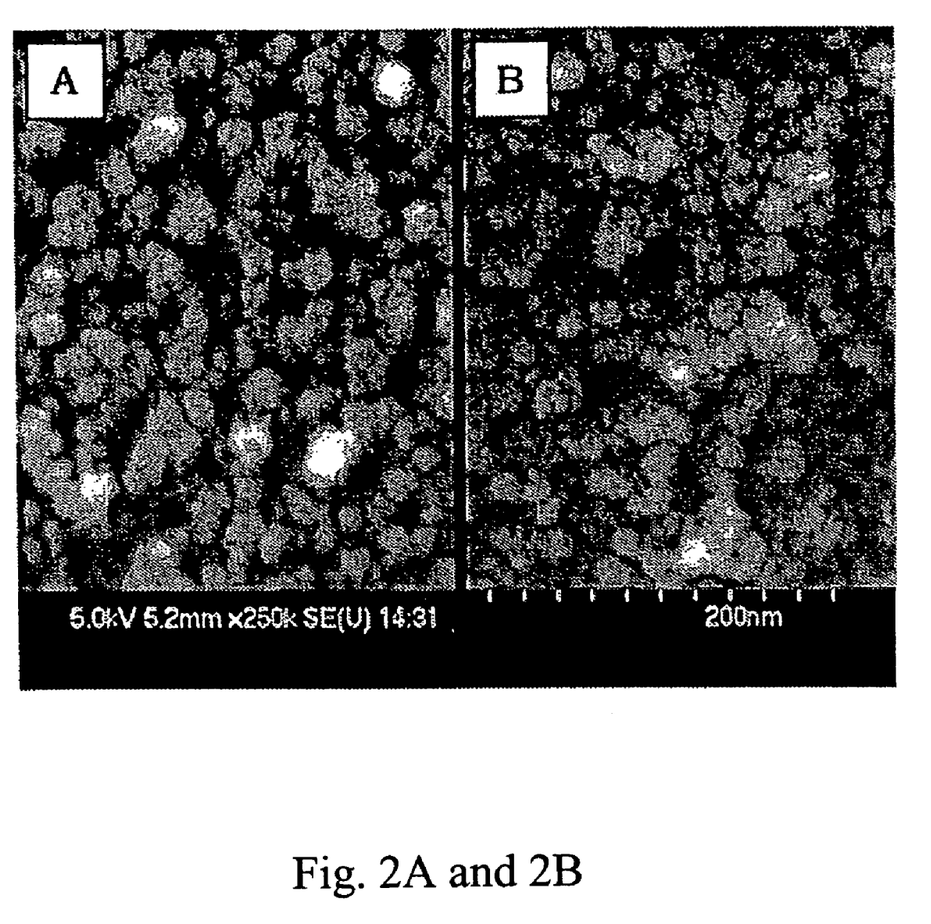
FIG. 2 shows SEM images from randomly selected spots in the interior of fractured monoliths of a native silica aerogel with $?_b$=0.169 g/cm$^{-3}$ (A) and a di-ISO cross-linked silica aerogel composite with $?_b$=0.380 g cm$^{-3}$ (B).

Base-catalyzed silica aerogels typically consist of large voids (mesopores, ~50 nm in diameter) in a "pearl-necklace" network of microporous, so-called secondary particles (Brinker and Scherer, Sol-Gel Science; The Physics and Chemistry of Sol-Gel Processing, Academic Press: New York, (1990)) which are the smallest entities visible in FIG. 2A (5-10 nm in diameter). Those particles are connected by "necks" formed by dissolution and reprecipitation of silica during aging (Brinker and Scherer, Sol-Gel Science; The Physics and Chemistry of Sol-Gel Processing, Academic Press: New York, (1990); Woignier and Phalippou, J. Non-Cryst. Solids, (1998) 100, 404-408). Reasonably, the strength of monolithic aerogels could be improved by making the necks wider. To accomplish this with minimum addition of new material, the contour surface of silica can be used as a template for the deposition and growth of the interparticle cross-linker.

Silica is surface-terminated with silanols (—SiOH). A polyurethane, (—CONH—R—NHCOOR'O—)$_n$, is formed by the reaction of a diisocyanate (OCN—R—NCO) and a diol (HO—R'—OH) (Smith and March, March's Advanced Organic Chemistry Reactions, Mechanism and Structure; John Wiley and Sons: New York, 2001). A similar reaction of an isocyanate cross-linking agent with the free hydroxyl groups of a sol-gel like material provides cross-linked aerogels having superior properties that allow them to be used in a large variety of applications.

I. General Preparation of Aerogels from Silicon Alkoxide Precursors

The formation of aerogels, in general, involves two major steps, the formation of a sol-gel like material, and the drying of the sol-gel like material to form an aerogel. Originally, sol-gel like materials were made by the aqueous condensation of sodium silicate, or a similar material. While this process worked well, the reaction formed salts within the gel that needed to be removed by many repetitive washings (a long, laborious procedure). With the rapid development of sol-gel chemistry over the last few decades, the vast majority of silica aerogels prepared today utilize silicon alkoxide precursors. The most common of these are tetramethyl orthosilicate (tetramethoxysilane, TMOS, $Si(OCH_3)_4$), and tetraethyl orthosilicate (tetraethoxysilane, TEOS, $Si(OCH_2CH_3)_4$). However, many other alkoxides, containing various organic functional groups, can be used to impart different properties to the gel. Alkoxide-based sol-gel chemistry avoids the formation of undesirable salt by-products, and allows a much greater degree of control over the final product. The balanced chemical equation for the formation of a silica gel from TEOS is:

$$Si(OCH_2CH_3)_{4\ (liq.)} + 2H_2O_{(liq.)} = SiO_{2\ (solid)} + 4HOCH_2CH_{3\ (liq.)}$$

The above reaction is typically performed in ethanol, with the final density of the aerogel dependent on the concentration of silicon alkoxide monomers in the solution. Note that the stoichiometry of the reaction requires two moles of water per mole of TEOS. In practice, this amount of water leads to incomplete reaction, and weak, cloudy aerogels. Most aerogel recipes, therefore, use a higher water ratio than is required by the balanced equation (anywhere from 4-30 equivalents).

Catalysts

The kinetics of the above reaction are impractically slow at room temperature, often requiring several days to reach completion. For this reason, acid or base catalysts are added to the formulation. The amount and type of catalyst used play key roles in the microstructural, physical and optical properties of the final aerogel product.

Acid catalysts can be any protic acid, such as HCl. Basic catalysis usually uses ammonia, or ammonia buffered with ammonium fluoride. Aerogels prepared with acid catalysts often show more shrinkage during supercritical drying and may be less transparent than base catalyzed aerogels. The microstructural effects of various catalysts are harder to describe accurately, as the substructure of the primary particles of aerogels can be difficult to image with electron microscopy. All generally show small (2-5 nm diameter) particles that are generally spherical or egg-shaped. With acid catalysis, however, these particles may appear "less solid" (looking something like a ball of string) than those in base-catalyzed gels. As condensation reactions progress, the sol will set into a rigid gel. At this point, the gel is usually removed from its mold. However, the gel should typically be kept covered by alcohol to prevent evaporation of the liquid contained in the pores of the gel. Evaporation causes severe damage to the gel and will lead to poor quality aerogels Single-Step vs. Two-Step Aerogels Typical acid or base catalyzed TEOS gels are often classified as "single-step" gels, referring to the "one-pot" nature of this reaction. A more recently developed approach uses pre-polymerized TEOS as the silica source. Pre-polymerized TEOS is prepared by heating an ethanol solution of TEOS with a sub-stoichiometric amount of water and an acid catalyst. The solvent is removed by distillation, leaving a viscous fluid containing higher molecular weight silicon alkoxides. This material is redissolved in ethanol and reacted with additional water under basic conditions until gelation occurs. Gels prepared in this way are known as "two-step" acid-base catalyzed gels. Pre-polymerized TEOS is available commercially in the United States from Silbond Corp. (i.e., Silbond® H-5).

These slightly different processing conditions impart subtle, but important changes to the final aerogel product. Single-step base catalyzed aerogels are typically mechanically stronger, but more brittle, than two-step aerogels. While two-step aerogels have a smaller and narrower pore size distribution and are often optically clearer than single-step aerogels.

Aging and Soaking

When a sol reaches the gel point, it is often assumed that the hydrolysis and condensation reactions of the silicon alkoxide reactant are complete. This is far from the case. The gel point simply represents the time when the polymerizing silica species span the container containing the sol. At this point the silica backbone of the gel contains a significant number of unreacted alkoxide groups. In fact, hydrolysis and condensation can continue for several times the time needed for gelation. Failure to realize, and to accommodate this fact is one of the most common mistakes made in preparing silica aerogels. Sufficient time must be given for the strengthening of the silica network. This can be enhanced by controlling the pH and water content of the covering solution. Common aging procedures for base catalyzed gels typically involve soaking the gel in an alcohol/water mixture of equal proportions to the original sol at a pH of 8-9 (ammonia). The gels are best left undisturbed in this solution for up to 48 hours.

This step, and all subsequent processing steps, are typically diffusion controlled. That is, transport of material into, and out of, the gel is unaffected by convection or mixing (due to the solid silica network). Diffusion, in turn, is affected by the thickness of the gel. In short, the time required for each processing step increases dramatically as the thickness of the gel increases.

After aging the sol-gel like material, all water still contained within its pores should be removed prior to drying. This is simply accomplished by soaking the sol-gel like material in a solvent, such as alcohol, several times until the water is removed. Again, the length of time required for this process is dependent on the thickness of the sol-gel like material. Any water left in the gel will not be removed by supercritical drying, and will lead to an opaque, white, and very dense aerogel.

Supercritical Drying

The final process in making silica aerogels is typically supercritical drying. This is where the liquid within the sol-gel like material is removed, leaving only the linked silica network. The process can be performed by venting the ethanol above its critical point (high temperature-very dangerous) or by prior solvent exchange with $CO_2$ followed by supercritical venting. This process should be performed in an autoclave specially designed for this purpose (small autoclaves used by electron microscopists to prepare biological samples are acceptable for $CO_2$ drying). The process is as follows. The sol-gel like materials are placed in the autoclave (which has been filled with ethanol). The system is pressurized to at least 750-850 psi with $CO_2$ and cooled to 5-10 degrees Celsius (C). Liquid $CO_2$ is then flushed through the vessel until all the ethanol has been removed from the vessel and from within the sol-gel like materials. When the sol-gel like materials are ethanol-free the vessel is heated to a temperature above the critical temperature and pressure of $CO_2$ (31° C. and 1050 psi respectively). As the vessel is heated the pressure of the system rises. The system is held at these conditions for a short time followed by the slow, controlled release of $CO_2$ to ambient pressure. As with previous steps, the length of time required for this process is dependent on the thickness of the gels. The process may last anywhere from a few hours to several days.

Figure 1:
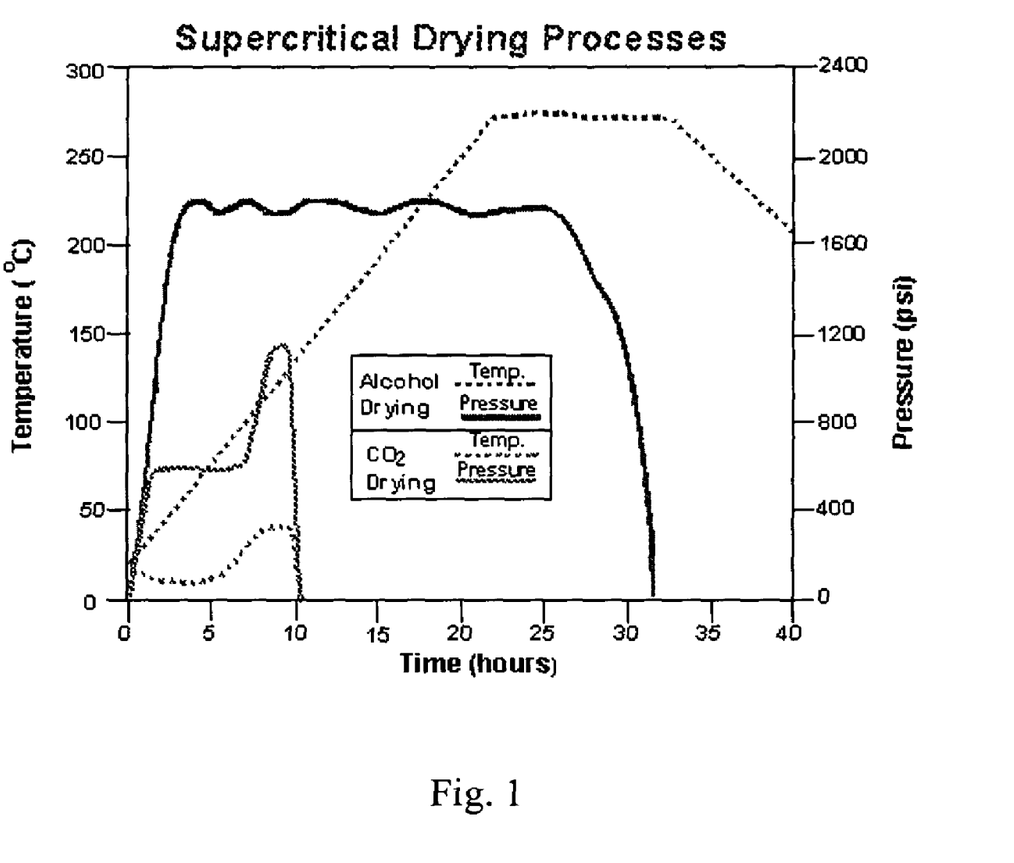
FIG. 1 illustrates the process conditions for both the carbon dioxide substitution/drying process, and the alcohol drying process.

FIG. 1 shows the process conditions for both the carbon dioxide substitution/drying process and the alcohol drying process.

A Procedure to Produce a Single-Step Base Catalyzed Silica Aerogel

The following procedure will produce an aerogel with a density of approx. 0.08 g/cm³. The gel time is approximately 60-120 minutes, depending on temperature.

A catalyst solution containing 35 mL of ethanol, 70 mL of water, 0.275 mL of 30% aqueous ammonia, and 1.21 mL of 0.5 M ammonium fluoride is slowly added to a silica solution containing 50 mL of TEOS and 40 mL of ethanol with stirring. The mixture of the catalyst solution and the silica solution is then poured into a mold until gelation. The gel can be processed as described above.

A Procedure to Produce a Two-step Acid-base Catalyzed Silica Aerogel

The following procedure will produce an aerogel with a density of approx. 0.08 g/cm³. The gel time is approximately 30-90 minutes, depending on temperature.

A catalyst solution containing 35 mL of ethanol, 75 mL of water, and 0.35 mL of 30% aqueous ammonia is slowly added to a silica solution containing 50 mL of precondensed silica (Silbond H-5, or equivalent) and 50mL of ethanol with stirring. The mixture of the catalyst solution and the silica solution is then poured into an appropriate mold until gelation. The gel can be processed as described above.

II. Cross-Linking Aerogels

General Procedure

A cross-linked aerogel can be produced by contacting a sol-gel like material with a cross-linking agent, and then drying the cross-linked sol-gel like material to produce a cross-linked aerogel. A sol-gel like material may be produced according to methods known in the art and disclosed herein. The sol-gel like material can be cross-linked by contacting the sol-gel like material with a solvent containing a cross-linking agent during the wash steps used during the production of an aerogel from the sol-gel like material.

In one example, a diisocyanate cross-linker is introduced into an aerogel structure as follows. Hydrogels (1 cm diameter, 3-4 cm long) are prepared from tetramethoxysilane via a base-catalyzed route and are aged for 2 days at room temperature (Leventis et al., Chem. Mater., 1999, 11, 2837-2845; Leventis et al., Nano. Lett., 2002, 2, 63-67). Subsequently, according to a post-gelation doping protocol, pores are filled with a diisocyanate (di-ISO) solution by washing successively with methanol, propylene carbonate (PC), and PC/di-ISO (4×8 h in each bath) (Leventis et al., Nano. Lett., 2002, 2, 63-67; Morris et al., Non-Cryst. Solids, 2001, 285, 29-36). The di-ISO employed was poly(hexamethylene diisocyanate) (Aldrich) or Desmodur 3200 (Bayer). The product specifications for the Aldrich di-ISO are monomer <0.5% w/w; isocyanate (NCO) group content was 23.1%. The theoretical NCO content for the dimer, $OCNCH_2(CH_2)_4CH_2NH(CO)O(CO)NH-CH_2(CH_2)_4CH_2NCO$, is 23.7%. The vials containing the gels in the last bath were heated at 100° C. for 3 days, then are cooled to room temperature. The solution was decanted, and the gels were washed with PC (1×8 h), PC/acetone (1:1, 1:3, v/v; 1×8 h each), and acetone (4×8 h) and were dried supercritically.

Cross-Linkers

Cross-linking agents within the scope of the invention include those compounds that are able to form a chemical bond with at least two reactive groups on a sol-gel material that can be made into an aerogel. For example, silica is surface-terminated with silanols (—SiOH). Thus, a cross-linking agent of the invention (A) includes those compounds having at least two reactive groups that can bond to at least two silanols on a gel-sol material (i.e., SiO—A–OSi). Examples of such reactive groups include, but are not limited to, activated bis acids such as bis(acid chlorides) and bis(acid anhydrides), where the acid can be a carboxylic acid, a phosphoric acid, a sulfonic acid, a sulfinic acid, or a phosphonic acid; diisocyanates, acid anhydrides, bis(acid anhydrides), acylchlorides, and bis(acylchlorides). Non-exclusive examples of diisocyanates are provided herein at Table III. Cross-linkers of the invention can have two reactive groups that are the same, or can have two reactive groups that are different from each other.

Cross-linkers of the invention also include compounds that react with each other to form a chemical linkage between two silanols on a sol-gel material. For example, a cross-linker (B) can bond to a single silanol group on a sol-gel material and to another cross-linker (C) that bonds to a single silanol group on the sol-gel material to form a chemical linkage between the two silanol groups (i.e., SiO—B—C—OSi).

Cross-linkers of the invention also include compounds that polymerize and form a chemical bond with reactive groups on a sol-gel material. For example, polyurethane is formed by the reaction of a diisocyanate with a diol. Thus, a diisocyanate may be used as a cross-linker in the presence of a diol such that polyurethane formation occurs until the chain is terminated upon bonding to a silanol on the sol-gel like material. Such a cross-linker will form urethane bonds in association with the cross-linked sol-gel like material. Urethane bonds of this type are thought to be useful for increasing the strength and resistance to breakage of cross-linked aerogels.

A cross-linker of the invention may also include an attached group that is bonded to a reactive group that bonds to a sol-gel material. An example of such a cross-linker is a diisocyanate (OCN—R—NCO) where R is an attached group that becomes chemically bonded to a sol-gel material through reaction of the isocyanates with the silanols on the sol-gel like material. Thus, the invention includes cross-linking agents having the same or different reactive groups linked to an attached group and that form a chemical bond with a reactive group on a sol-gel like material. An example of an attached group includes a phosphate group that would be useful as a fire retardant if chemically bonded to an aerogel. Additional examples of attached groups include, but are not limited to, absorbants, catalysts, flurophores, biomolecules, redox active labels, reactive groups such as amines, epoxides, hydroxyls, anhydrides, acylhalides, and carboxyl groups.

The methods and materials of the invention do not include those described or prepared according to the disclosure of Yim et al., *Korean J. Chem. Eng.*, 19:159-166 (2002) or Mizushima and Hori, *J. Non-Cryst. Solids*, 170:215-222 (1994).

III. Preparation of Cross-linked Aerogel Films

Cross-linked aerogel films can be prepared from the cross-linked aerogels described herein. Such films may be prepared by forming a sol-gel like material on a surface where the sol-gel like material forms a film. Examples of such surfaces include, but are not limited to, plastic, metal, metal foil, or surfaces that have been coated, for example, through use of a sputtering process. A surface can be made of a material that dissolves in a solvent to which a cross-linked aerogel is resistant. Such a surface may be used as a support to form a cross-linked aerogel film and then dissolved to free the film from the support.

The sol-gel material can be processed into a cross-linked aerogel while contained on a surface. For example, the sol-gel material can be washed with a desired solvent, treated with a cross-linking agent, and dried to produce a cross-linked aerogel while contained on a surface. Such a process should allow rapid production of cross-linked aerogel films due to the large surface area of the film relative to the thickness of the film. This feature allows solvents to be rapidly vaporized.

Cross-linked aerogel films offer many benefits because they will have a large surface area. For example, a cross-linking agent that contains an attached group that is a catalyst may be used to produce an aerogel film having a catalyst cross-linked to the surface. Such a film may be useful in the production of catalytic converters in the automotive industry or in the production of catalyst supports in the chemical industry. In another example, a cross-linking agent that contains an absorbant as an attached group may by linked to the film to produce a film having a very large absorbant surface area.

IV. Properties of Cross-linked Aerogels

Diisocyanate (di-ISO) modified aerogels are often translucent (FIG. 3), with properties (Table II) that depend on their density, which in turn depends on the concentration of di-ISO in the PC/di-ISO bath. Relative to native silica, composite aerogels may shrink by up to 10-12% and they often become up to ~3 times more dense as the di-ISO concentration in the bath increases. Both size and density level off for bathing solutions more concentrated than ~40% w/w, but even the most dense monoliths fall in the density range of aerogels. Shrinking is probably associated with cross-linking. IR analysis shows that as the density increases, the urethane C=O stretch (at ~1690 $cm^{-1}$) becomes comparable to, and eventually even stronger than, the Si—O stretch at 1078 $cm^{-1}$. Note also that while the urethane C=O stretch is present in di-ISO, the dominant stretch at ~2272 $cm^{-1}$ comes from the isocyanate (N=C=O) (Husing et al., Chem. Mater., 1998, 10, 3024-3032). However, the latter absorption is consistently extremely weak or absent. Therefore, it was concluded that both ends of practically all di-ISO have reacted. A typical SEM image of one of the most dense composites (FIG. 2B) shows that (a) a new material has been introduced conformally to the secondary particles, as not only the necklace-like structure but also individual particles remain clearly visible; and (b) the mesoporocity has been somewhat reduced, as several secondary particles appear fused (clustered) together, forming the larger domains that promote light scattering and haziness (Novak et al., Chem. Mater., 1994, 6, 282-286). These observations are all consistent with reaction and binding of di-ISO to the surface of silica. Considering the total surface area of native silica (~1000 g $cm^{-3}$, Table II) and the density change between native silica and the most dense composite ($\rho_b$=0.447 g $cm^{-3}$), it is calculated that the amount of di-ISO corresponds to 4.7 monolayers. Hence, terminal NCOs appear to undergo not only condensation with surface-silanols but also further reaction with themselves causing extensive cross-linking. It should be emphasized further that the estimated 4.7 monolayer coverage is actually a lower limit, because the first monolayer blocks the channels and cuts off access to the micropores of the secondary particles. This is concluded from the fact that the Brunauer-Emmett-Teller (BET) surface area decreases, and the average pore diameter jumps from ~13 to ~20 nm as the monolith density increases (Table II).

Figure 3:
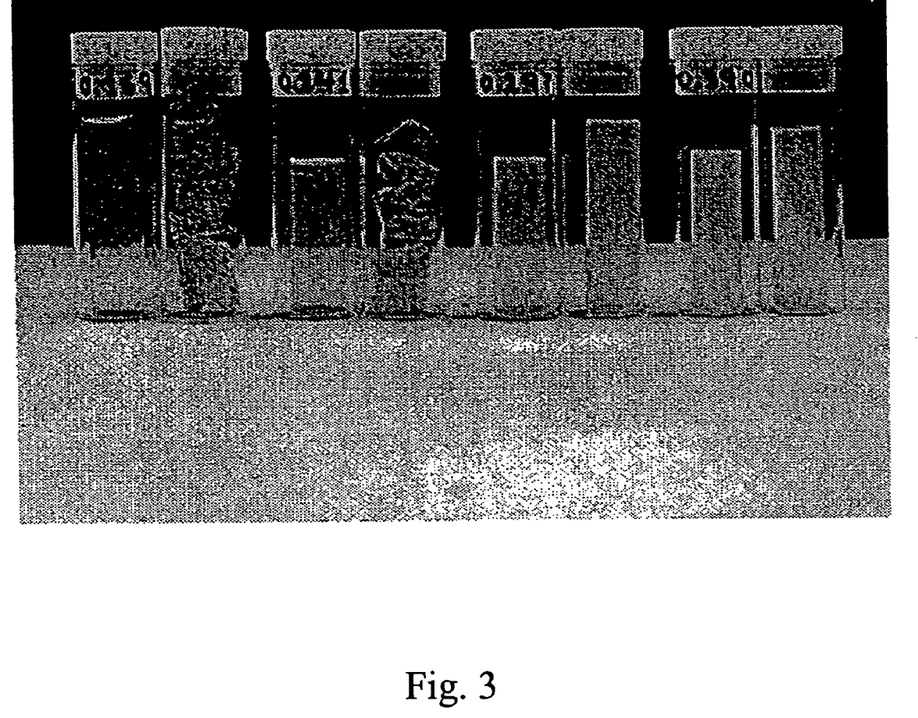
FIG. 3 illustrates photographs of four pairs of aerogel monoliths (diameter: 0.9-1.0 cm; length: 3-4 cm; densities in g cm$^{-3}$ are reported directly on the vials and include 0.169; 0.141; 0.297 and 0.390). The left-most sample ($?_b$=0.169 g cm$^{-3}$) is native silica. The right vial of each pair contains a similar-density aerogel that has been submerged in liquid $N_2$ in a drybox.

Composite monoliths are less hygroscopic and more robust than pure silica (Table II). Native silica aerogels submerged in liquid $N_2$ (in a glovebox) absorb ~6.5 times their weight in liquified gas (which they subsequently lose over a period of ~10 min). At the same time, however, those monoliths undergo extensive cracking, losing their structural integrity completely (FIG. 3). Cracking was also observed consistently with all samples of the lighter composite ($\rho_b$=0.241 g cm$^{-3}$), but the mode of fracture was different from that of native silica, yielding few large pieces with structural integrity rather than the loose foamy material obtained from the disintegration of the latter. Composites with $\rho_b$>0.3 g cm$^{-3}$ uptake, <1.7 times their weight in liquid $N_2$, but no structural change were observed, even after repetitive dip-freeze/thaw cycling. The structural collapse of pure silica aerogels in contact with liquids is a known phenomenon and is due to the capillary tension at the liquid-gas interface in the pores (Fricke, Sci. Am., 1998 (March) 92-97). An upper bound for the volume relaxation energy, VRE (in J cm$^{-3}$), upon collapse is calculated from the work done per unit volume by the capillary tension via the relationship $$VRE=\gamma_{LV}\cos(\theta)[A\rho_a/(1-\rho)]$$

by assuming that the contact angle $\theta=0°$ and that the pore liquid is water (whose surface tension $\gamma_{LV}$=0.072 J m$^{-2}$ is higher than that of many other liquids), A is the specific (BET) surface area of the aerogel, and the relative density $\rho \approx 0.3$ (Brinker and Scherer; Sol-Gel Science; The Physics and Chemistry of Sol-Gel Processing, Academic Press: New York, 1990). Thus, it is calculated that upon collapse our native aerogel monoliths are stabilized by ≦17 J cm$^{-3}$. Meanwhile, considering the mass-gain over silica of our most dense composite (0.447 g cm$^{-3}$) and the heats of formation of dicarbamate and isocyanurate, it is calculated that the composite is more stable than native silica by ~55 J cm$^{-3}$. This was calculated based on a 4.7 monolayer coverage (7.85×10-4 mol of di-ISO per cm3), where half of the NCOs of the first monolayer from urethane with the surface silanols, releasing (based on bond heats of formation) 61 kJ per mol of di-ISO reacting, while all other NCO groups in the remaining 3.7 monolayers form isocyanurate, releasing 32 kJ per mol of NCO. Therefore, there should be no particular tendency for collapse upon wetting, because the energy that would be expended to destroy cross-linking is more than the energy that would be gained by the subsequent structural collapse. Even in water, denser composites have been stable for at least two months.

Figure 4:
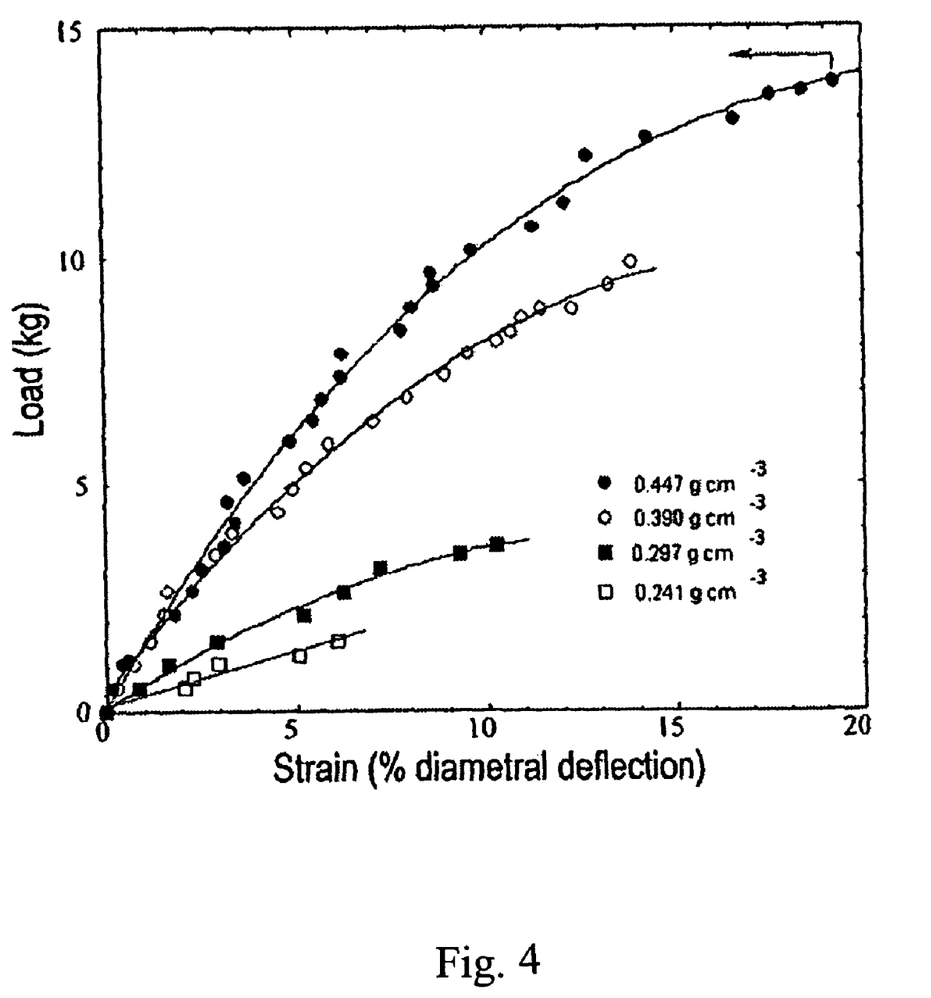
FIG. 4 is a graph illustrating load-strain curves for the four composites of FIG. 3. The arrow correlates the particular data point with the image in FIG. 5.
Figure 5:
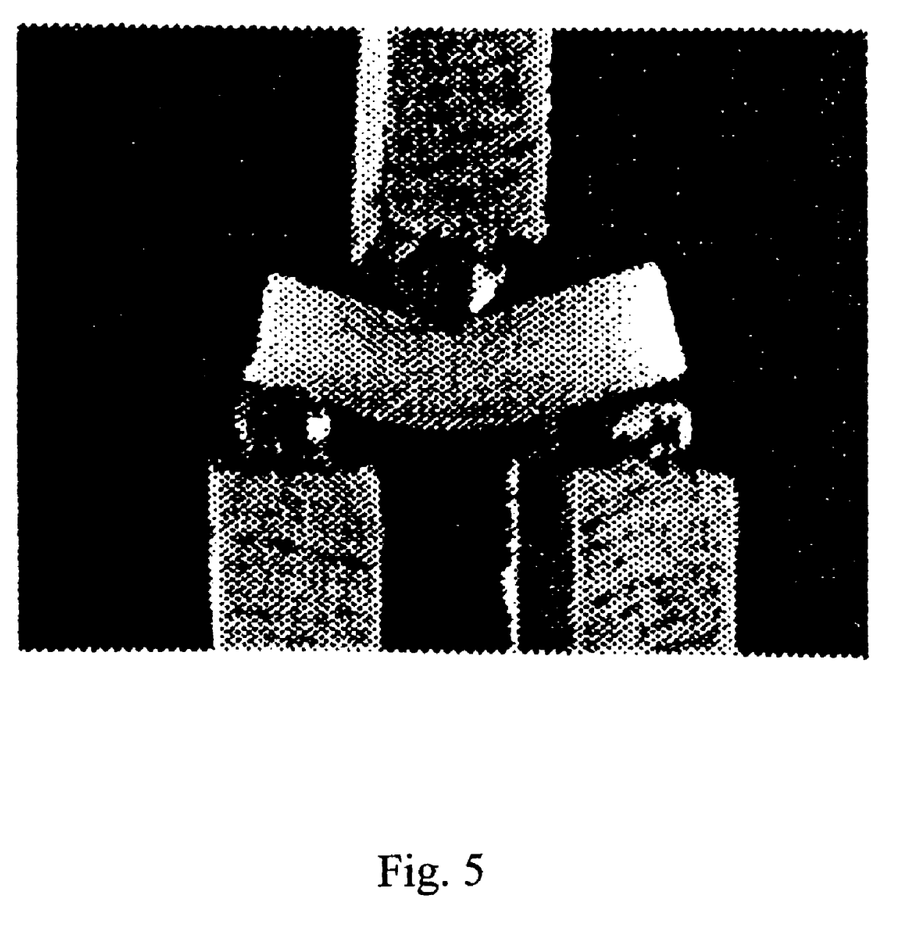
FIG. 5 illustrates bending under a 14.4 kg load of the monolith with $?_b$=0.447 g cm$^{-3}$; span=1.738 cm).
Figure 6:
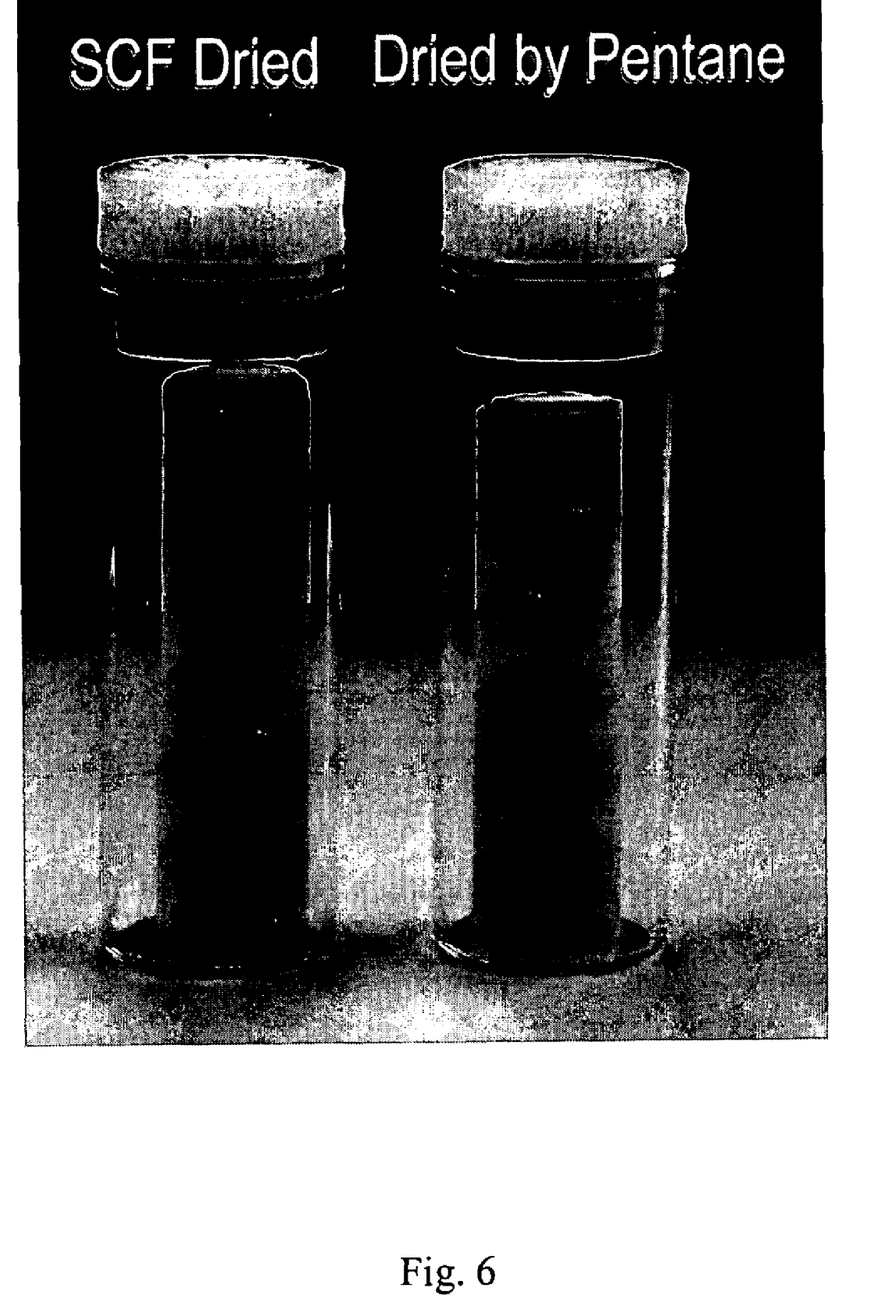
FIG. 6 illustrates photographs of two aerogel monoliths. The left-most sample was supercritical fluid extraction (SCF) dried, and the right-most sample was pentane dried at ambient pressure.

However, the most dramatic improvement yet is in the strength of the new material (Table II), as tested with a three-point flexural bending method. It takes more than 100 times higher load to break a monolith with density 0.447 g cm$^{-3}$ (~15 kg) than to break a native silica aerogel monolith (~120 g). FIG. 4 shows the load-strain curves of four representative composite monoliths on the way to their respective rupture points. The least dense sample is linearly elastic, while the more dense samples behave as nonlinear elastic. Removing the load at several points before samples fail does not have an adverse effect in their ability to resume their previous shape or accept back the same load, producing the same deformation and continuing along the smooth lines of FIG. 4. The modulus of elasticity, E, (a measure of stiffness) is calculated from the slope (S) of the linear part of the load-deformation curves using $$E=SL^3/12\pi r^4$$

where L is the span and r the radius of the aerogel (Gere and Timoshenko, Mechanics of Materials, 4th ed.; PWS Publishing: Boston, 1997). Measuring the deformation of native silica was not possible; however, accepting that for a native silica aerogel with $\rho_b$=0.2 g cm$^{-3}$ and E≦1.0 MPa, the trend in the modulus of the cross-linked monoliths is the same as the trend in the rupture load (Novak et al., Chem. Mater., 1994, 6, 282-286). Namely, more dense monoliths are not only stronger but also more difficult to bend (stiffer). This is consistent with wider interparticle necks as the amount of accumulated di-ISO increases (Iler, The Chemistry of Silica; Wiley: New York, (1979)). Eventually, even the stiffer composites bend, accommodating up to 20% diametral deflections before rupture (see FIG. 5). The more work (i.e., the area underneath the load/deformation curve) required by denser composites to break indicates that stiffer composites are also tougher. This behavior is attributed to the flexible organic nature of the wider necks.

In summary, molecular-level synergism between silica nanoparticles and molecular cross-linkers inverts the relative host-guest roles in glass-polymer composites, leading to new strong low-density materials. Attempts to load gels with variable amounts of polyurethane precursors such as di-ISO and diol end-capped polybutylene adipate followed by heat treatment, washing, and supercritical drying led to opaque materials, somewhat stronger than silica but still quite brittle and much inferior to the materials described above. Direct mixing of a diisocyanate and an alcohol-free sol has been attempted recently by Yim et al., Korean J. Chem. Eng., 19:159-166 (2002) and Mizushima and Hori, J. Non-Cryst. Solids, 170: 215-222 (1994). Reportedly, these procedure lead to week-long gelation times and require an at least equally long aging period. In the attempt to add various amounts of di-ISO in a base-catalyzed sol in PC, a week-long gelation time was noticed. The resulting aerogels were translucent but no less brittle than native silica.

Further studies are underway to (a) reduce the processing time by replacing PC with less viscous solvents and oven heating with microwave heating; (b) vary the chemical identity of the diisocyanate, as well as the composition and density of silica; and (c) cross-link the few residual NCO groups by introducing appropriate diols (Javni et al., Polym. Mater. Sci. Eng., 2002, 86, 387-388).

V. Uses of Cross-linked Aerogels

The cross-linked aerogels described herein may be used in a large number of applications that are exemplified below. These include structural applications where cross-linked aerogels may be used as light-weight building materials, or to reinforce plastics and other materials used in construction. The cross-linked aerogels may also be used to produce more durable optical sensors, such as those used to detect oxygen. Radiation detectors may also be made from the cross-linked aerogels described herein. The resistance of the cross-linked aerogels to structural collapse makes them useful in fuel storage cells. In one example, a phosphate group may be incorporated into a sol-gel like material to produce a fire retardant cross-linked aerogel. Such an aerogel may be used within a fuel cell to provide structural support as well as protection against fires. Cross-linked aerogels may also be used as supports, such as for absorbants and catalysts.

The cross-linked aerogels may also be subjected to pyrolysis to coat the aerogels with carbon. Such a carbon-coated silica aerogel would be suitable as a dimensionally stable electrode material for electrolysis, double layer capacitors for storing electrical charge, or as a low density dielectric. Thus, cross-linked aerogels can be incorporated into integrated circuits. A cross-linked carbon-coated aerogel could also be used in the field of superconductivity. For example, the cross-linked aerogels do not collapse in the presence of liquid nitrogen or other liquefied gasses. Thus, carbon-coated cross-linked aerogels may be used in conjunction with a liquefied gas under conditions of extreme cold to conduct an electric current.

The increased strength of cross-linked aerogels allows them to be used as structural materials. Examples of structural applications for cross-linked aerogels include the production of produce building materials such as ceiling tiles, floor tiles, doors, paneling, shingles, shutters, beams, and the like. The cross-linked aerogels may be used in the automotive and aerospace industry due to their strength and light weight. Examples of such uses include automotive and aircraft panels, seats, flooring, handles, levers, and the like. The cross-linked aerogels can also be used to create protective clothing such as bullet-proof vests, jackets, and helmets; and heat resistant clothing articles.

The cross-linked aerogels can also be used in numerous applications as insulating materials due to their thermal properties. For example, the cross-linked aerogels can be used in the manufacture of refrigerator doors and panels, oven doors and panels, coolers, clothing, clothing liners, shoes, boots, insulation panels, and the like.

EXAMPLES

Example I

Preparation of Diisocyanate Cross-linked Tetramethoxysilane Sol-gel Monoliths

The contents of two vials: Vial A: 4.514 mL of tetramethoxysilane; 3.839 mL of methanol; and Vial B: 4.514 mL of methanol; 1.514 mL water and 20 μL (microliter) of concentrated ammonium hydroxide, were mixed thoroughly to form the sol, which was poured in polyethelene cylindrical vials (1 cm diameter, 5 cm long). The molds were covered with parafilm®. To facilitate removal of the gels from the polyethylene molds, the bottom cup was covered with a teflon-tape lining. The sol gels in the molds at room temperature in about 10 min, and the resulting gels are left in the molds to age (i.e., complete polymerization and cross-linking) for 2 days. Subsequently, the bottom covers of the molds were removed together with the teflon lining, and the gels were pushed gently out of their molds directly into vials filled with methanol (one gel per vial).

The pores of the gel was then filled with a diisocyanate solution by washing the gel four times for eight hours per wash with methanol, propylene carbonate, and then a mixture containing propylene carbonate and poly(hexamethylene diisocyanate) in succession. During the last wash, the gels were heated to 100° C. for three days, and were then cooled to room temperature. The wash solution was decanted and the gels were washed with propylene carbonate one time for eight hours. The gels were then washed in a mixture of propylene carbonate and acetone (1:1, v/v) one time for eight hours, followed by washing in a mixture of propylene carbonate and acetone (1:3, v/v) one time for eight hours. The gels were then washed in acetone four times for eight hours per wash. Following the acetone wash, the gels were dried supercritically with carbon dioxide.

Example II

Alternate Preparation of Diisocyanate Tetramethoxysilane Sol-gel Monoliths

The tetramethoxysilane sol-gel monolith was prepared as described in Example I except that the wash conditions were altered according to the following procedure. The gels were prepared and aged for two days as described above, and then washed four times in methanol for eight hours per wash. The gels were then washed four times in acetone for eight hours per wash. The gels were then washed in a mixture of acetone and poly(hexamethylene diisocyanate) (1:1, v/v) four times for eight hours per wash. The gels were then maintained in the last wash solution at 50°C. for four days in tightly capped vials. Following the heating period, the gels were washed four times with acetone for eight hours per wash, and then dried supercritically with carbon dioxide.

Example III

Preparation of Aerogels Without Supercritical Drying

The cross-linked aerogels of the invention are resistant to collapse when contacted with fluids. Therefore, the need to process a cross-linked sol-gel by supercritical drying to form a cross-linked aerogel is unnecessary. Accordingly, a cross-linked sol-gel material was prepared by following the protocol described in Example I, except that the supercritical drying step was avoided. Rather, the cross-linked aerogels were washed in pentane four times for twelve hours per wash. The cross-linked aerogels were then removed from the pentane and placed into an oven that was heated to 40° C. The gels were completely dried in one hour. The properties of the air-dried aerogels are similar to those of aerogels prepared using supercritical fluid extraction are presented below in Table I.

TABLE I

Properties of Supercritical Fluid Extraction (SCF) dried and Pentane dried aerogels

|  | Supercritical Fluid Dried | Pentane Dried |
|---|---|---|
| Density (g/cm$^{-3}$) | 0.57 +/− 0.02 | 0.56 +/− 0.01 |
| BET Surface Area (m$^2$/g) | 150 +/− 10 | 132 +/− 15 |
| Average Pore Diameter (Å) | 194 +/− 6 | 185 +/− 20 |
| Modulus (MPa) | 67 +/− 23 | 75 +/− 22 |
| Load at Rupture (kg) | 34 +/− 8 | 34 +/− 9 |

Example IV

Preparation of a Cross-linked Aerogel Film

Thin films can be prepared from the cross-linked aerogels described herein. Such films may be prepared by thoroughly mixing the contents of two vials: Vial A: 4.514 mL of tetramethoxysilane; 3.839 mL of propylene carbonate; and Vial B: 4.514 mL of propylene carbonate; 1.514 mL water and 20 μL (microliter) of concentrated ammonium hydroxide, to form a sol. The sol is then poured onto a gold coated glass plate. The sol-gel material contained on the surface of the plate is then evenly distributed on the plate by spinning the plate. The plate containing the sol-gel material is quickly dipped in propylene carbonate to wash the sol-gel material.

The plate containing the sol-gel material is then placed into a container containing a mixture of propylene carbonate and diisocyanate and heated in a microwave oven. Following heating, the plate containing the cross-linked sol-gel material is quickly washed in propylene carbonate, washed in another desired solvent, and then allowed to dry. The gold coated plate is placed into a solution of potassium cyanide to dissolve the gold film and release the cross-linked aerogel from the plate.

TABLE II

Properties of Silica/Di-ISO Aerogel Monoliths

| % di-ISO w/w in the bath | diameter[b] (cm) | $\rho_b$[b] (g cm$^{-3}$) | BET area (m$^2$ g$^{-1}$) (Av. pore diam, nm) | hydrophilicity[d] | load at rupture[e] (kg) | diametral deflection at rupture[f] (cm) | modulus of elasticity (E)[g] (Mpa) |
|---|---|---|---|---|---|---|---|
| 0.0 | 0.999 ± 0.002 | 0.169 ± 0.004 | 997 (13.4)[c] | 66 ± 16 | 0.12 (h) | h | h |
| 4.0 | 0.999 ± 0.002 | 0.241 ± 0.003 | 324 (i) | 16 ± 2 | 1.75 (i) | 0.061 | 5.3 (i) |
| 8.0 | 0.986 ± 0.010 | 0.297 ± 0.007 | 308 (18.1) | 8 ± 2 | 3.95 (4.38) | 0.101 | 12.5 (10.5) |
| 16 | 0.954 ± 0.011 | 0.388 ± 0.006 | 309 (22.3) | 4 ± 1 | 9.65 (9.73) | 0.140 | i (20.4) |
| 25 | 0.936 ± 0.007 | 0.390 ± 0.013 | 245 (21.9) | 4 ± 1 | 10.4 (9.87) | 0.129 | 31.3 (26.1) |
| 34 | 0.908 ± 0.013 | 0.440 ± 0.009 | 215 (23.2) | 5 ± 2 | 8.70 (9.87) | 0.110 | i (40.1) |
| 42 | 0.907 ± 0.006 | 0.447 ± 0.020 | 165 (16.6) | 5 ± 1 | 14.7 (15.6) | 0.199 | 47.5 (46.3) |
| 51 | 0.897 ± 0.014 | 0.439 ± 0.016 | 178 (29.8) | 4 ± 2 | 12.0 (11.8) | 0.109 | i (53.8) |

[a]Native silica.
[b]Average of four samples.
[c]Average of two samples with respective spreads ±3 m$^2$ g$^{-1}$ and ±1 nm.
[d]Percent weight gain after three days in a water vapor saturated chamber at room temperature. Average of two samples.
[e]Results from two three-point flexural bending test experiments using: (a) a homemade apparatus (1.738 cm span, see FIG. 5) (ASTM Designation Standard: D 2344/D 2344M-00, Annual Book of ASTM Standard, Vol. 15.03, 2000) or, (in parentheses) (b) an automated Instron Instument Model 4469 (2.286 cm span). The two series of samples for the two tests were prepared by two experimentalists at different times. Tests with the homemade apparatus were carried out with four different series of variable-density monoliths, and all loads at rupture at each density were within 5% of their average. Diametral deflection vs load, however, was recorded (see footnote f) for only a single series of samples (the one reported). The Instron test was also carried out with a single series of variable-density monoliths (the one reported).
[f]Determined by analyzing close-up images obtained from a fixed distance with a Nikon CoolPix 5000 digital camera set in the macro mode and 2× electronic magnification. Actual deflections were calculated by multiplying deflections measured on 8.5 in. × 11 in. prints by the experimentally determined aspect ratio (0.136).
[g]Calculated (see text) either from the slopes of the linear part of the curves in FIG. 4, or from the slopes given by the Instron output.
[h]Beyond the capabilities of either apparatus.
[i]Not determined.

TABLE III

Examples of diisocyanates cross-linking agents

1. Hexamethylene diisocyanate (HDI)

OCN~~~~~~NCO

And polymers thereof (e.g., Desmodur ® N-3200):

OCN~~~~~~NH(CO)O(CO)NH~~~~~~NCO

2. Methylene diisocyanate (MDI)

OCN-⌬-CH$_2$-⌬-NCO

And polymers thereof (e.g., Desmodur ® E-22; polyMDI):

OCN-[⌬-CH$_2$-⌬-NH(CO)O(CO)NH-⌬-CH$_2$-⌬]$_n$-NCO (Av. n = 2)

3. Toluene diisocyanate monomer. For example Desmodur ® TD 80, which is a

TABLE III-continued

Examples of diisocyanates cross-linking agents mixture of:
4. Triphenyl methyl triisocyanate (e.g., Desmodur ® RE)

5. Desmodur ® W, a monomer with structure:

1. Other cross-linking agents include the structures listed in Table II where the OCN group is replaced with other reactive groups that will react with free —OH groups on a sol-gel like material.
2. Desmodurs ® are commercially available from the Bayer corporation.

Documents

Hench, L. L.; West, J. K. *Chem. Rev.* 1990, 90, 33-72.
Husing, N.; Schubert, U. *Angew. Chem., Int. Ed. EngL.* 1998, 37, 22-45.
Fricke, *J. Sci. Am.* 1988 (March), 92-97.
Fricke, J.; Arduini-Schuster, M. C.; Buttner, D.; Ebert, H.-P.; Heinemann, U.;
Hetfleisch, J.; Hummer, E.; Kuhn, J.; Lu, X. In *Thermal Conductivity* 21; Cremers, C. J., Fine, H. A., Eds.; Plenum Press: New York 1990; pp 235-245.
Pajonk, G. M. *Catal. Today* 1999,52, 3-13.
Morris, C. A.; Anderson, M. L.; Stroud, R. M.; Merzbacher, C. I.; Rolison, D. R. *Science* 1999, 284, 622-624.
Novak, B. M.; Auerbach, D.; Verrier, C. *Chem. Mater.* 1994, 6, 282-286.
*Chem & Eng. News* 2002 (Jan. 28), pp 21-22.
Parmenter, K. E.; Milstein, F. *J. Non-Cryst. Solids* 1998, 223, 179-189.
Brinker, C. J.; Scherer, G. W. *Sol-Gel Science; The Physics and Chemistry of Sol-Gel Processing*, Academic Press: New York, 1990: (a) pp 531-536; (b) p 362, 391; (c) pp 465-468.
Woignier, T.; Phalippou, J. *J. Non-Cryst. Solids* 1988, 100, 404-408.
Smith, M. B.; March, J. *March's Advanced Organic Chemistry Reactions, Mechanism and Structure*; John Wiley and Sons: New York, 2001; (a) pp 1182-1183, (b) p 24.
Yosomiya, R.; Morimoto, K.; Suzuki, T. *J. Appl. Polym. Sci.* 1984, 29, 671-679.
Ray, S.; Frei, R. -W. *J. Chromatogr.* 1972, 71, 451-457.
Kang, S.; Il Hong, S.; Choe, C. R.; Park, M.; Rim, S.; Kim, J. *Polymer* 2001, 42, 879-887.
Leventis, N.; Elder, I. A.; Rolison, D. R.; Anderson, M. L.; Merzbacher, C. *Chem. Mater.* 1999, 11, 2837-2845.
Leventis, N.; Elder, I. A.; Long, G. J.; Rolison, D. R. *Nano Lett.* 2002, 2, 63-67.
Morris, C. A.; Rolison, D. R.; Swider-Lyons, K. E.; Osbum-Atkinson, E. J.; Merzbacher, C. I. *J. Non-Cryst. Solids* 2001, 285, 29-36.
Husing, N.; Schubert, U.; Misof, K.; Fratzl, P. *Chem. Mater.* 1998, 10, 3024-3032.
Spirkova, M. *J. Appl. Polymer Sci.* 2002, 85, 84-91.
Okumoto, S.; Yamabe, S. *J. Comput. Chem.* 2001, 22, 316-326.
Gere, J. M.; Timoshenko, S. P. *Mechanics of Materials*, 4th ed.; PWS Publishing: Boston, 1997; pp 599-607, 870, 885.
Iler, R. K. *The Chemistry of Silica*; Wiley: New York, 1979; pp 222-230, and 519-523.
Yim, T. -J.; Kim, S. Y.; Yoo, K. -P. *Korean J. Chem. Eng.* 2002, 19, 159-166.
Javni, I.; Zhang, W.; Petrovic, Z. S. *Polym. Mater. Sci. Eng.* 2002, 86, 387-388.
Rettelbach, R., J. Sauberlich, S. Korder, and J. Fricke 1995 Thermal Conductivity of Ir-Opacified Silica Aerogel Powders Between 10 K and 275 K. *Journal ofphysics D-Applied Physics* 28:581-587.
Rettelbach, T., J. Sauberlich, S. Korder, and J. Fricke 1995 Thermal Conductivity of Silica Aerogel Powders At Temperatures From 10 to 275 K. *Journal of Non-Crystalline Solids* 186:278-284.

Hrubesh, L. W., and J. F. Poco 1995 Thin Aerogel Films For Optical, Thermal, Acoustic and Electronic Applications. *Journal of Non-Crystalline Solids* 188:46-53.

Hrubesh, L. W., and R. W. Pekala 1994 Thermal properties of organic and inorganic aerogels. *Journal of Materials Research* 9:731-738.

Zeng, S. Q., A. J. Hunt, W. Cao, and R. Greif 1994 Pore size distribution and apparent gas thermal conductivity of silica aerogel. *Journal of Heat Transfer* 116:756-759.

Reiss, H. 1992 Heat transfer in thermal insulations. *Physikalische Blaetter* 48:617-622.

Bernasconi, A., T. Sleator, D. Posselt, J. K. Kjems, and H. R. Ott 1992 Low-Temperature Specific Heat and Thermal Conductivity of Silica Aerogels. *Journal of Non-Crystalline Solids* 145:202-206.

Scheuerpflug, P., M. Hauck, and J. Fricke 1992 Thermal Properties of Silica Aerogels Between 1.4-K and 330-K. *Journal of Non-Crystalline Solids* 145:196-201.

Bernasconi, A., T. Sleator, D. Posselt, J. K. Kjems, and H. R. Ott 1992 Dynamic Properties of Silica Aerogels As Deduced From Specific-Heat and Thermal-Conductivity Measurements. *Physical Review B-Condensed Matter* 45:10363-10376.

Posselt, D., J. K. Kjems, A. Bernasconi, T. Sleator, and H. R. Ott 1991 The Thermal Conductivity of Silica Aerogel In the Phonon, the Fracton and the Particle-Mode Regime. *Europhysics Letters* 16:59-65.

Scheuerpflug, P., H. J. Morper, G. Neubert, and J. Fricke 1991 Low-Temperature Thermal Transport In Silica Aerogels. *Journal of Physics D-Applied Physics* 24:1395-1403.

Xianping, Lu, Wang Peng, D. Buettner, U. Heinemann, O. Nilsson, J. Kuhn, and J. Fricke 1991 Thermal transport in opacified monolithic silica aerogels. *High Temperatures High Pressures* 23:431-436.

Sleator, T., A. Bernasconi, D. Posselt, J. K. Kjems, and H. R. Ott 1991 Low-Temperature Specific Heat and Thermal Conductivity of Silica Aerogels. *Physical Review Letters* 66:1070-1073.

Caps, R., G. Doll, J. Fricke, U. Heinemann, and J. Hetfleisch 1989 Thermal Transport In Monolithic Silica Aerogel. *Journal De Physique* 50: C4113-C4118.

Fricke, J., 1989 Thermal insulation without CFC. *Physik in Unserer Zeit* 20:189-191.

Fricke, J., E. Hummer, H. J. Morper, and P. Scheuerpflug 1989 Thermal Properties of Silica Aerogels. *Journal De Physique* 50: C487-C497.

Buettner, D., R. Caps, U. Heinemann, E. Huemmer, A. Kadur, and J. Fricke 1988 Thermal loss coefficients of low-density silica aerogel tiles. *Sol. Energy* 40:13-15.

Fricke, J., R. Caps, D. Buettner, U. Heinemann, E. Huemmer, and A. Kadur 1987 Thermal loss coefficients of monolithic and granular aerogel systems. *Sol. Energy Mater.* 16:267-274.

Hrubesh, L. W., and J. F. Poco 1995 Thin Aerogel Films For Optical, Thermal, Acoustic and Electronic Applications. *Journal of Non-Crystalline Solids* 188:46-53.

Zhu, L., Y. F. Li, J. Wang, and J. Shen 1995 Structural and Optical Characteristics of Fullerenes Incorporated Inside Porous Silica Aerogel. *Chemical Physics Letters* 239:393-398.

Emmerling, A., R. Petricevic, A. Beek, P. Wang, H. Scheller, and J. Fricke 1995 Relationship Between Optical Transparency and Nanostructural Features of Silica Aerogels. *Journal of Non-Crystalline Solids* 185:240-248.

Beck, A., W. Koerner, and J. Fricke 1994 Optical investigations of granular aerogel fills. *Journal of physics. D, Applied Physics* 27:13-18.

Hotaling, S. P. 1993 Ultra-Low Density Aerogel Optical Applications. *Journal of Materials Research* 8:352-355.

Emmerling, A., P. Wang, G. Popp, A. Beck, and J. Fricke 1993 Nanostructure and Optical Transparency of Silica Aerogels. *Journal De Physique Iv* 3:357-360.

Platzer, W. J., and M. Bergkvist 1993 Bulk and surface light scattering from transparent silica aerogel. *Solar Energy Materials and Solar Cells* 31:243-251.

Wang, P., W. Korner, A. Emmerling, A. Beck, J. Kuhn, and J. Fricke 1992 Optical Investigations of Silica Aerogels. *Journal of Non-Crystalline Solids* 145:141-145.

Beck, A., O. Gelsen, P. Wang, and J. Fricke 1989 Light Scattering For Structural Investigations of Silica Aerogels and Alcogels. *Journal De Physique* 50: C4203-C4208.

Lampert, C. M., 1987 Advanced optical materials for energy efficiency and solar conversion. *Sol. Wind TechnoL* 4:347-379.

Hunt, A. J., and P. Berdahl 1984 Structure data form light scattering studies of aerogel. *Mater. Res. Soc. Symp. Proc.:* 275-280.

Lampert, C. N. 1983 Solar optical materials for innovative window design. *Int. J Energy Res.* 7:359-374.

Hunt. A. J., and Ayers, M. R. 2001 Investigations of Silica Alcogel Using Coherent Light. *Journal of Non-Crystalline Solids,* 285:162-166.

Woignier, T., J. Phalippou, H. Hdach, G. Larnac, F. Pernot, and G. W. Scherer 1992 Evolution of Mechanical Properties During the Alcogel Aerogel Glass Process. Journal of Non-Crystalline Solids 147:672-680.

Armand, A. C., and D. Guyomar 1992 Acoustic and Mechanical Characterization of Silica Aerogels. *Journal De Physique Iii* 2:759-762.

Hdach, H., T. Woignier, J. Phalippou, and G. W. Scherer 1990 Effect of Aging and pH On the Modulus of Aerogels. *Journal of Non-Crystalline Solids* 121:202-205.

Woignier, T., and J. Phalippou 1989 Scaling Law Variation of the Mechanical Properties of Silica Aerogels. *Journal De Physique* 50: C4179-C4184.

Phalippou, J., T. Woignier, and R. Rogier 1989 Fracture Toughness of Silica Aerogels. *Journal De Physique* 50: C4191-C4196.

Cross, J., R. Goswin, R. Gerlach, and J. Fricke 1989 Mechanical Properties of SiO2-Aerogels. *Journal De Physique* 50: C41 85-C4190.

Adachi, I., T. Sumiyoshi, K. Hayashi, N. Iida, R. Enomoto, K. Tsukada, R. Suda, S. Matsumoto, K. Natori, M. Yokoyama, and H. Yokogawa 1995 Study of a threshold Cherenkov counter based on silica aerogels with low refractive indices. *Nuclear Instruments and Methods in Physics Research, Section A* 355:390-398.

Ganezer, K. S., W. E. Keig, and A. F. Shor 1994 A simple high efficiency Cherenkov counter. *IEEE Transactions on Nuclear Science* 41:336-342.

Hasegawa, T., O. Hashimoto, T. Nagae, and M. Sekimoto 1994 A large silica aerogel Cherenkov counter for SKS. *Nuclear Instruments and Methods in Physics Research, Section A* 342:383-388.

Brajnik, D., S. Korpar, G. Medin, M. Staric, and A. Stanovnik 1994 Measurement of Sr-90 Activity With Cherenkov Radiation In a Silica Aerogel. *Nuclear Instruments & Methods In Physics Research Section a-Accelerators Spectrometers Detectors and Associated Equipment* 353:217-221.

Fields, D. E., H. Vanhecke, J. Boissevain, B. V. Jacak, W. E. Sondheim, J. P. Sullivan, W. J. Willis, K. Wolf, E. Noteboom, P. M. Peters, and R. Burke 1994 Use of Aerogel For Imaging Cherenkov Counters. *Nuclear Instruments &*

*Methods In Physics Research Section a-Accelerators Spectrometers Detectors and Associated Equipment* 349:431-437.

Adachi, Ichiro 1994 R and D on Cherenkov counter based on silica aerogel with low refractive index. *Hoshasen* 20:21-30.

Lippert, C., R. Siebert, J. P. Didelez, J. Ernst, R. Frascaria, J. Y. Martel, and R. Skowron 1993 Particle discrimination in medium energy physics with an aerogel Cherenkov detector. *Nuclear Instruments and Methods in Physics Research, Section A* 333:413-421.

Onuchin, A., A. Shamov, Yu Skovpen, A. Vorobiov, A. Danilyuk, T. Gorodetskaya, and V. Kuznetsov 1992 The aerogel Cherenkov counters with wavelength shifters and phototubes. *Nuclear Instruments and Methods in Physics Research, Section A* 315:517-520.

Miskowiec, D., W. Ahner, E. Grosse, P. Senger, and W. Walus 1990 Aerogel Cherenkov detectors for the Kaon spectrometer. *Verhandlungen der Deutschen Physikalischen Gesellschaft* 25:1520.

Vincent, P., R. Debbe, A. Pfoh, and M. Abreu 1988 E802 aerogel Cherenkov detector. *Nucl. Instrum. Methods Phys. Res.* 272:660-668.

Carlson, P. 1986 Aerogel Cherenkov counters: Construction principles and applications. *Nucl. Instrum. Methods Phys. Res.* 248:110-117.

Poelz, G. 1986 Aerogel Cherenkov counters at DESY. *Nucl. Instrum. Methods Phys. Res., Sect. A.* 248:118-129.

Kawai, H., J. Haba, T. Homma, M. Kobayashi, K. Miyake, T. S. Nakamura, N. Sasao, Y. Sugimoto, M. Yoshioka, and M. Daigo 1985 Tests of a silica aerogel Cherenkov counter. *Nucl. Instrum. Methods Phys. Res., Sect. A* 228:314-322.

Maurer, K., G. Koebschall, K. Roehrich, C. Schmitt, and V. H. Walther 1984 Silica aerogel threshold Cherenkov counters for use at intermediate energies. *Nucl. Instrum. Methods Phys. Res., Sect. A* 224:110-111.

Fernandez, C., K. E. Johansson, M. Schouten, S. Tavernier, P. Ladron de Guevara, P. Herquet, J. Kesteman, and O. Pingot 1984 Performance of the silica aerogel Cherenkov detector used in the European Hybrid Spectrometer. *Nucl. Instnim. Methods Phys. Res., Sect. A* 225:313-318.

Yasumi, Shinjiro, and Hideyuki Kawai 1983 Silica aerogel Cherenkov counter. *Nippon Butsuri Gakkaishi* 38:671-676.

Poelz, G., and R. Riethmueller 1982 Preparation of silica aerogel for Cherenkov counters. *Nucl. Instrum. Methods Phys. Res.* 195:491-503.

Carlson, P. J., K. E. Johansson, J. Norrby, J. Kesteman, O. Pingot, S. Tavernier, and L. van Lancker 1982 Tests of an 18 module silica aerogel Cherenkov detector to be used in the European hybrid spectrometer. *Nucl. Instrum. Methods Phys. Res.* 192:209-216.

Burkhardt, H., P. Koehler, R. Riethmueller, B. H. Wiik, R. Fohrmann, J. Franzke, H. Krasemann, R. Maschuw, G. Poelz, and J. Reichardt 1981 TASSO gas and aerogel Cherenkov counters. *Nucl. Instrum. Methods* 184:319-331.

Trachsel, C., D. Perrin, and R. Schwarz 1981 Study of an aerogel Cherenkov detector with indirect light collection. *Helv. Phys. Acta* 53:655-661.

de Brion, J. P., A. Caillet, J. B. Cheze, J. Derre, G. Marel, E. Pauli, and C. Pigot 1981 Silica aerogel Cherenkov counter in a missing-mass experiment K/sup−/d . . . > . . . K/sup+/+X at 1.4 GeV/c. *Nucl. Instrum. Methods* 179:61-65.

Carlson, P. J., K. E. Johansson, J. Kesteman, O. Pingot, J. Norrby, S. Tavernier, F. van den Bogaert, and L. van Lancker 1979 Increased photoelectron collection efficiency of a photomultiplier in an aerogel Cherenkov counter. *Nucl. Instrum. Methods* 160:407-410.

Bourdinaud, M., J. B. Cheze, and J. C. Thevenin 1976 Use of silica aerogel for Cherenkov radiation counter. *Nucl. Instrum. Methods* 136:99-103.

Coddens, G., J. Dekinder, and R. Millet 1995 Time-of-Flight Inelastic Neutron Scattering Study of Liquid He-4 In Silica Aerogels. *Journal of Non-Crystalline Solids* 188:41-45.

Ehrburgerdolle, F., J. Dallamano, E. Elaloui, and G. M. Pajonk 1995 Relations Between the Texture of Silica Aerogels and Their Preparation. *Journal of Non-Crystalline Solids* 186:9-17.

Hua, D. W., J. Anderson, J. Digregorio, D. M. Smith, and G. Beaucage 1995 Structural Analysis of Silica Aerogels. *Journal of Non-Crystalline Solids* 186:142-148.

Jarzebski, A. B., and J. Lorene 1995 Pore Network Connectivity and Effective Diffusivity of Silica Aerogels. *Chemical Engineering Science* 50:357-360.

Rogacki, G., and P. Wawrzyniak 1995 Diffusion of Ethanol-Liquid CO2 In Silica Aerogel. *Journal of Non-Crystalline Solids* 186:73-77.

Tsou, P. 1995 Silica Aerogel Captures Cosmic Dust Intact. *Journal of Non-Crystalline Solids* 186:415-427.

Yokogawa, H., and M. Yokoyama 1995 Hydrophobic Silica Aerogels. *Journal of Non-Crystalline Solids* 186:23-29.

Zhu, L., Y. F. Li, J. Wang, and J. Shen 1995 Intense Visible Light Emission From Fullerene-Doped Silica Aerogel. *Journal of Applied Physics* 77:2801-2803.

Zhu, L., Y. F. Li, J. Wang, and J. Shen 1995 Structural and Optical Characteristics of Fullerenes Incorporated Inside Porous Silica Aerogel. *Chemical Physics Letters* 239:393-398.

Schaefer, D. W., B. J. Olivier, C. Ashley, G. Beaucage, D. Richter, B. Farago, B. Frick, and D. A. Fischer 1994 Structure and Topology of Silica Aerogels During Densification. *Journal of Non-Crystalline Solids* 172:647-655.

Bruesch, P., F. Stucki, T. Baumann, P. Klugeweiss, B. Bruhl, L. Niemeyer, R. Strumpler, B. Ziegler, and M. Mielke 1993 Electrical and Infrared Dielectrical Properties of Silica Aerogels and of Silica Aerogel-Based Composites. *Applied Physics a-Solids and Surfaces* 57:329-337.

Gross, J., T. Schlief, and J. Fricke 1993 Ultrasonic Evaluation of Elastic Properties of Silica Aerogels. *Materials Science and Engineering a-Structural Materials Properties Microstructure and Processing* 168:235-238.

Igarashi, K, K. Tajiri, Y. Tai, and S. Tanemura 1993 Structural Study By Dsc, Saxs, and Raman Spectroscopy of Silica Aerogel. *Zeitschrift Fur Physik D-Atoms Molecules and Clusters* 26:S207-S209.

Kralj, S., G. Lahajnar, A. Zidansek, N. Vrbancickopac, M. Vilfan, R. Bline, and M. Kosec 1993 Deuterium Nmr of a Pentylcyanobiphenyl Liquid Crystal Confined In a Silica Aerogel Matrix. *Physical Review E* 48:340-349.

Pauthe, M., F. Despetis, and J. Phalippou 1993 Hydrophobic Silica CO2 Aerogels. *Journal of Non-Crystalline Solids* 155:110-114.

Buckley, A. M., and M. Greenblatt 1992 The Preparation and Characterisation of Silica Aerogels and Xerogels Doped With Transition Metal Species. *Journal of Non-Crystalline Solids* 146:97-110.

Buckley, A. M., and M. Greenblatt 1992 A Comparison of the Microstructural Properties of Silica Aerogels and Xerogels. *Journal of Non-Crystalline Solids* 143:1-13.

Courtens, E., and R. Vacher 1992 Structure and Dynamics of Silica Aerogels. *Philosophical Magazine B-Physics of Condensed Matter Structural Electronic Optical and Magnetic Properties* 65:347-355.

Damrau, U., H. C. Marsmann, O. Spormann, and P. Wang 1992 Si-29 Mas-Nmr Investigations of Silica Aerogels. *Journal of Non-Crystalline Solids* 145:164-167.

Dasilva, A., P. Donoso, and M. A. Aegerter 1992 Properties of Water Adsorbed In Porous Silica Aerogels. *Journal of Non-Crystalline Solids* 145:168-174.

Duval, E., A. Boukenter, T. Achibat, B. Champagnon, J. Serughetti, and J. Dumas 1992 Structure of Silica Aerogels and Vibrational Dynamics In Fractal Materials and Glasses—Electron Microscopy and Low-Frequency Raman Scattering. *Philosophical Magazine B-Physics of Condensed Matter Structural Electronic Optical and Magnetic Properties* 65:181-189.

Ehrburgerdolle, F., M. Holz, C. Mauzac, J. Lahaye, and G. M. Pajonk 1992 Characterization of the Porous Texture of Aerogel, Precipitated and Pyrogenic Silicas. *Journal of Non-Crystalline Solids* 145:185-190.

Foret, M., A. Chougrani, R. Vacher, and J. Pelous 1992 From Colloidal-Silica Sols to Aerogels and Xerogels. *Journal De Physique Iv* 2:135-139.

Gross, J., and J. Fricke 1992 Ultrasonic Velocity Measurements In Silica, Carbon and Organic Aerogels. *Journal of Non-Crystalline Solids* 145:217-222.

Posselt, D., J. S. Pedersen, and K. Mortensen 1992 A Sans Investigation On Absolute Scale of a Homologous Series of Base-Catalysed Silica Aerogels. *Journal of Non-Crystalline Solids* 145:128-132.

Schaefer, D. W., B. J. Olivier, C. S. Ashley, D. Richter, B. Farago, B. Frick, L. Hrubesh, M. J. Vanbommel, G. Long, and S. Krueger 1992 Structure and Topology of Silica Aerogels. *Journal of Non-Crystalline Solids* 145:105-112.

Emmerling, A., R. Gerlach, R. Goswin, J. Gross, G. Reichenauer, J. Fricke, and H. G. Haubold 1991 Structural Modifications of Highly Porous Silica Aerogels Upon Densification. *Journal of Applied Crystallography* 24:781-787.

Crowell, P. A., G. K. S. Wong, and J. D. Reppy 1990 Measurement of the Superfluid Density In Silica Aerogels. *Physica B* 165:549-550.

Devreux, F., J. P. Boilot, F. Chaput, and B. Sapoval 1990 Nmr Determination of the Fractal Dimension In Silica Aerogels. *Physical Review Letters* 65:614-617.

Jang, K. Y., and K. Kim 1990 Study of sol—gel processing for fabrication of hollow silica—aerogel spheres. *Journal of Vacuum Science and Technology, A* 8:1732-1735.

Jang, K. Y., K. Kim, and R. S. Upadhye 1990 Study of Sol-Gel Processing For Fabrication of Hollow Silica-Aerogel Spheres. *Journal of Vacuum Science & Technology a-Vacuum Surfaces and Films* 8:1732-1735.

Phalippou, J., T. Woignier, and M. Prassas 1990 Glasses From Aerogels.1. the Synthesis of Monolithic Silica Aerogels. *Journal of Materials Science* 25:3111-3117.

Schaefer, D. W., C. J. Brinker, D. Richter, B. Farago, and B. Frick 1990 Dynamics of Weakly Connected Solids—Silica Aerogels. *Physical Review Letters* 64:2316-2319.

Woignier, T., J. Phalippou, R. Vacher, J. Pelous, and E. Courtens 1990 Different Kinds of Fractal Structures In Silica Aerogels. *Journal of Non-Crystalline Solids* 121: 198-201.

Boukenter, A., D. Champagnon, J. Dumas, E. Duval, J. F. Quinson, J. L. Rousset, J. Serughetti, S. Etienne, and C. Mai 1989 A Saxs Study of Silica Aerogels. *Journal De Physique* 50: C4133-C4136.

Kim, N. K., K. Kim, D. A. Payne, and R. S. Upadhye 1989 Fabrication of hollow silica aerogel spheres by a droplet generation method and sol—gel processing. *J. Vac. Sci. Technol., A* 7:1181-1184.

Maynard, R., R. Calemczuk, A. M. Degoer, B. Salce, J. Bon, E. Bonjour, and A. Bourret 1989 Low Energy Excitations In Silica Aerogels. *Journal De Physique* 50: C4107-C4112.

Schaefer, D. W. 1989 What Factors Control the Structure of Silica Aerogels. *Journal De Physique* 50: C4121-C4126.

Mukherjee, S. P., J. F. Cordaro, and J. C. Debsikdar 1988 Pore structures and microstructures of silica gel monoliths at different stages of sintering. *Advanced Ceramic Materials* 3:463-467.

Fearon, E. M., P. R. Coronado, R. G. Garza, D. H. Darling, and P. C. Souers 1987 Shrinkage and opacity of 100 kg/m$^3$ silica aerogel foam in liquid deuterium-tritium. *J. Nucl. Mater.* 149:105-108.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A porous cross-linked metal oxide or silicon oxide based aerogel material produced by:
   (a) first, forming a metal oxide or silicon oxide based sol-gel preformed material prior to reaction with an organic cross-linking agent,
   (b) contacting the metal oxide or silicon oxide based sol-gel preformed material with an organic cross-linking agent in an amount comprising at least about 2% by weight based on the total weight of the cross-linked metal oxide or silicon oxide based sol-gel material, the cross-linking agent comprising an organic compound that provides an organic surface layer chemically bound to surfaces of said metal oxide or silicon oxide based sol-gel preformed material and then,
   (c) drying the metal oxide or silicon oxide based sol-gel preformed material provided with the surface layer of chemically bound organic material to form the porous cross-linked metal oxide or silicon oxide based aerogel material.

2. A cross-linked metal oxide or silicon oxide based sol-gel material, comprising
   a metal oxide or silicon oxide based sol-gel preformed material that has been formed prior to reaction with an organic cross-linking agent, said metal oxide or silicon oxide based sol-gel preformed material having a surface layer of an organic substance formed by chemical bonding of an organic cross-linking agent in an amount comprising at least about 2% by weight based on the total weight of the cross-linked metal oxide or silicon oxide based sol-gel material to surfaces of said metal oxide or silicon oxide based sol-gel preformed material after formation of said metal oxide or silicon oxide based sol-gel preformed material so as to form said cross-linked metal oxide or silicon oxide based sol-gel material.

3. The cross-linked metal oxide or silicon oxide based sol-gel material of claim 2, wherein the cross-linking agent comprises at least about 5% by weight based on the total weight of the cross-linked metal oxide or silicon oxide based sol-gel material.

4. The cross-linked metal oxide or silicon oxide based sol-gel material of claim 2, wherein the cross-linking agent comprises at least about 10% by weight based on the total weight of the cross-linked metal oxide or silicon oxide based sol-gel material.

5. The cross-linked metal oxide or silicon oxide based sol-gel material of claim 2, wherein the cross-linking agent comprises at least about 30% by weight based on the total weight of the cross-linked metal oxide or silicon oxide based sol-gel material.

6. The cross-linked metal oxide or silicon oxide based sol-gel material of claim 2, wherein the cross-linking agent comprises at least about 50% by weight based on the total weight of the cross-linked metal oxide or silicon oxide based sol-gel material.

7. The cross-linked metal oxide or silicon oxide based sol-gel material of claim 2, wherein the cross-linking agent comprises at least about 80% by weight based on the total weight of the cross-linked metal oxide or silicon oxide based sol-gel material.

8. The sol-gel material of claim 2, wherein the preformed metal oxide or silicon oxide based sol-gel material is silica based.

9. The cross-linked metal oxide or silicon oxide based sol-gel material of claim 2, wherein the cross-linking agent is a diisocyanate, a triisocyanate, a polyisocyanate, or a mixture thereof.

10. The cross-linked metal oxide or silicon oxide based sol-gel material of claim 2, wherein the cross-linking agent is hexamethylene diisocyanate, poly(hexamethylene diisocyanate), toluene diisocyanate, diphenylmethane diisocyanate, an aliphatic polyisocyanate, triphenylmethyl triisocyanate, or a mixture thereof.

11. The cross-linked metal oxide or silicon oxide based sol-gel material of claim 2, wherein the cross-linked metal oxide or silicon oxide based sol-gel material is more resistant to rupture under load than the preformed metal oxide or silicon oxide based sol-gel material prior to cross-linking with the cross-linking agent.

12. A cross-linked metal oxide or silicon oxide based aerogel material formed by drying of the cross-linked metal oxide or silicon oxide based sol-gel material of claim 2, the drying being carried out using at least one of solvent exchange, supercritical drying, or a process that does not involve supercritical drying.

13. The aerogel material of claim 12 wherein the aerogel material does not collapse when in contact with a liquid that comprises water, an alcohol, an ether, a hydrocarbon, an ester, a ketone, a carboxylic acid, a phosphoric acid, or a liquefied gas.

14. The cross-linked metal oxide or silicon oxide based aerogel material of claim 13, wherein the liquefied gas is nitrogen, argon, helium, hydrogen, or oxygen.

15. The cross-linked metal oxide or silicon oxide based aerogel material of claim 13, wherein the hydrocarbon is kerosene, gasoline, jet fuel, or rocket fuel.

16. A thermal insulating material comprising the sol-gel material of claim 2.

17. A tile, door, panel, shingle, shutter, beam, cooler, article of clothing, shoe, or boot comprising the thermal insulating material according to claim 16.

18. A structural material comprising the material of claim 2.

19. The metal oxide or silicon oxide based sol-gel material of claim 2 wherein a chemical functionality of the surfaces of said metal oxide or silicon oxide based sol-gel material acts as a template for reaction with, accumulation of, or both, the cross-linking agent.

20. The metal oxide or silicon oxide based sol-gel material of claim 2 wherein the surfaces of the metal oxide or silicon oxide based sol-gel material act as a template for the cross-linking agent.

21. The sol-gel material of claim 2 comprising an attached group wherein the cross-linking agent comprising an organic compound includes the attached group.

\* \* \* \* \*